US012644092B2

(12) United States Patent
Vann

(10) Patent No.: US 12,644,092 B2
(45) Date of Patent: Jun. 2, 2026

(54) MULTI-LEVEL MACHINE LEARNING FOR PREDICTIVE AND PRESCRIPTIVE APPLICATIONS

(71) Applicant: Applied Materials, Inc., Santa Clara, CA (US)

(72) Inventor: Lucas Richard Vann, Raleigh, NC (US)

(73) Assignee: Applied Materials, Inc., Santa Clara, CA (US)

( * ) Notice: Subject to any disclaimer, the term of this patent is extended or adjusted under 35 U.S.C. 154(b) by 1088 days.

(21) Appl. No.: 17/191,078

(22) Filed: Mar. 3, 2021

(65) Prior Publication Data

US 2022/0282199 A1    Sep. 8, 2022

(51) Int. Cl.
*C12M 1/36* (2006.01)
*C12M 1/24* (2006.01)
(Continued)

(52) U.S. Cl.
CPC ............ *C12M 41/48* (2013.01); *C12M 23/08* (2013.01); *C12M 41/38* (2013.01); *C12M 41/46* (2013.01); *G16B 40/00* (2019.02)

(58) Field of Classification Search
CPC ...... C12M 41/48; C12M 23/08; C12M 41/38; C12M 41/46; G16B 40/00
See application file for complete search history.

(56) References Cited

U.S. PATENT DOCUMENTS

2012/0077219 A1    3/2012  Ma et al.
2012/0107921 A1    5/2012  Willson et al.
(Continued)

FOREIGN PATENT DOCUMENTS

EP        3778860 A1      2/2021
WO     2020089922 A1      5/2020
WO     2020260229 A1     12/2020

OTHER PUBLICATIONS

Nanna Petersen Rønnest, et al., Introducing process analytical technology (PAT) in filamentous cultivation process development: comparison of advanced online sensors for biomass measurement, Journal of Industrial Microbiology and Biotechnology, vol. 38, Issue 10, Oct. 1, 2011., (Year: 2011).*
(Continued)

*Primary Examiner* — Larry D Riggs, II
*Assistant Examiner* — Emilie A Smith
(74) *Attorney, Agent, or Firm* — Lowenstein Sandler LLP

(57) ABSTRACT

The subject matter of this specification can be implemented in, among other things, methods, systems, computer-readable storage medium. A method can include receiving cell growth data with a current cell culture of a cell growth system. The cell growth data includes growth input parameter values indicative of a growth rate of the current cell culture. The method can further include identifying, using a first machine learning model, a prescriptive action to alter a yield of a target product of the current cell culture based on the cell growth data. The prescriptive action modifies a metabolism rate of the current cell culture. The method further includes performing at least one of displaying the identified prescriptive on a graphical user interface (GUI) and/or causing the cell growth system to perform the identified prescriptive action.

18 Claims, 7 Drawing Sheets

*200*

(51) Int. Cl.
  *C12M 1/34*          (2006.01)
  *G16B 40/00*        (2019.01)

(56)              References Cited

U.S. PATENT DOCUMENTS

| | | |
|---|---|---|
| 2020/0377844 A1 | 12/2020 | Paul et al. |
| 2021/0035655 A1 | 2/2021 | Tanouchi et al. |
| 2021/0262047 A1* | 8/2021 | Mccready .............. G16B 40/00 |

OTHER PUBLICATIONS

Mesquita T. J.B., Campani, G., Giordano, R.C., Zangirolami, T. C., & Horta, A. C. Machine learning applied for metabolic flux-based control of micro-aerated fermentations in bioreactors. Biotechnology and Bioengineering. 2021; 118: 2076-2091. (Year: 2021).*

Stephen Gang Wu et al., ""Rapid Prediction of Bacterial Heterotrophic Fluxomics Using MachineLearning and Constraint Programming"", PLOS Computational Biology 12(4): e1004838, pp. 1-22, Apr. 19, 2016, pp. 2-17, pp. 1-22.

G. Panagiotou et al., ""Monitoring novel metabolic pathways using metabolomics and machinelearning: induction of the phosphoketolase pathway in Aspergillus nidulans cultivations"", Metabolomics, vol. 3, No. 4, pp. 503-516, Dec. 2007.

International Search Report and Written Opinion for International application No. PCT/US2022/016427, mailed May 26, 2022, 10 pages.

Extended European Search Report for European Application No. 22763750.1, mailed Dec. 3, 2025, 8 Pages.

* cited by examiner

300

Growth Prediction Model

Feeding Rate                                                        Cell Volume

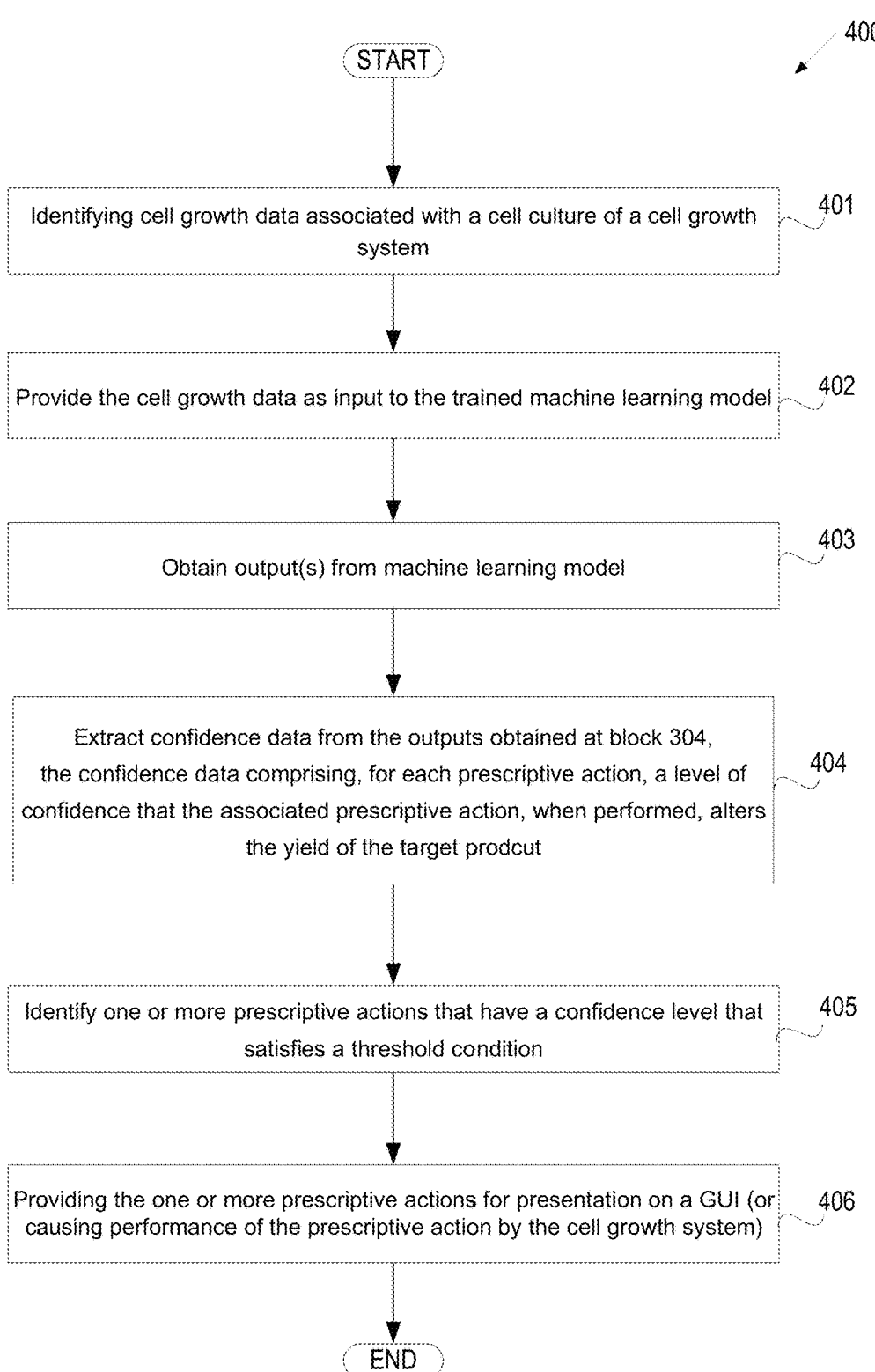

400

START

Identifying cell growth data associated with a cell culture of a cell growth system ⟋401

Provide the cell growth data as input to the trained machine learning model ⟋402

Obtain output(s) from machine learning model ⟋403

Extract confidence data from the outputs obtained at block 304, the confidence data comprising, for each prescriptive action, a level of confidence that the associated prescriptive action, when performed, alters the yield of the target prodcut ⟋404

Identify one or more prescriptive actions that have a confidence level that satisfies a threshold condition ⟋405

Providing the one or more prescriptive actions for presentation on a GUI (or causing performance of the prescriptive action by the cell growth system) ⟋406

END

FIG. 4

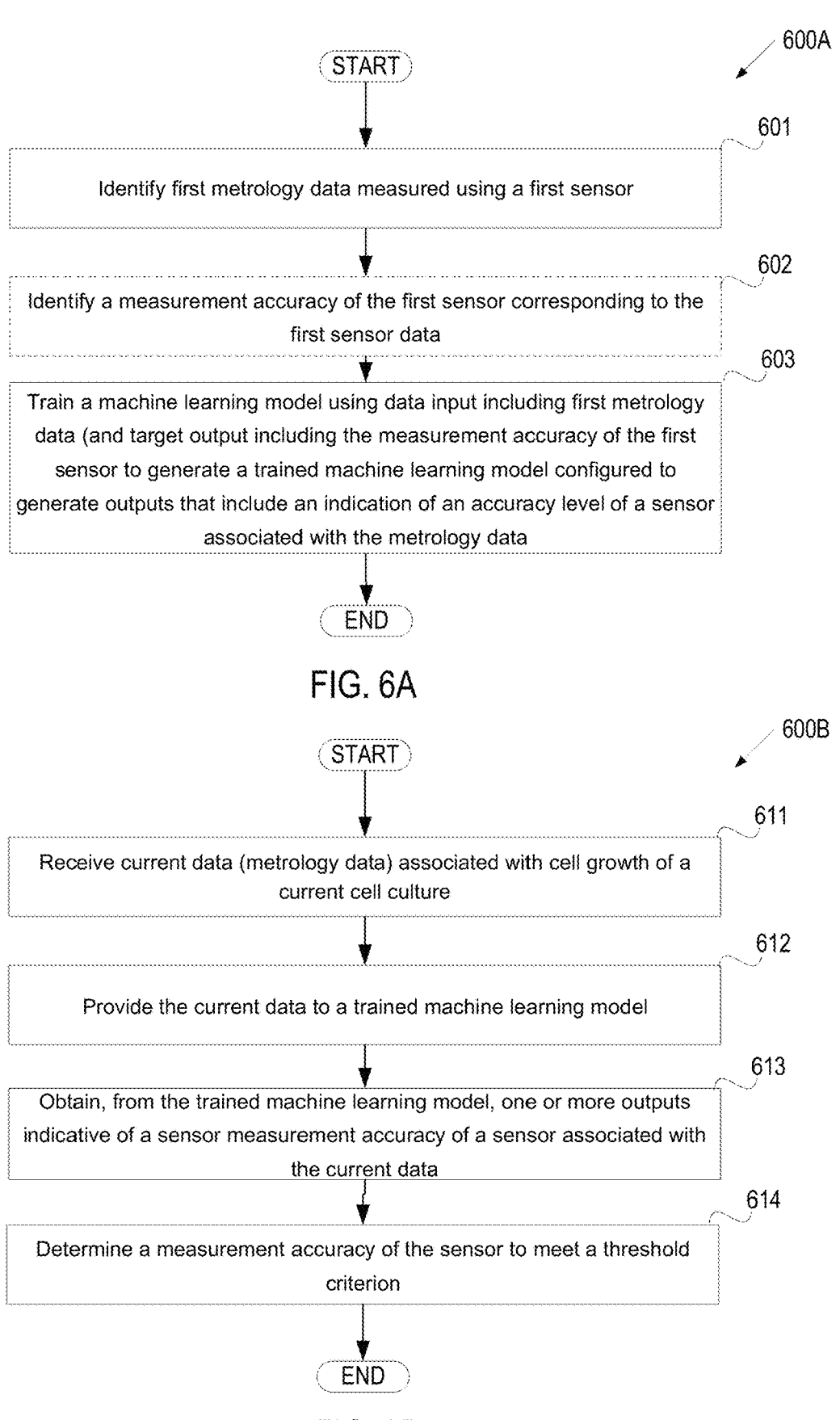

600A

START

601

Identify first metrology data measured using a first sensor

602

Identify a measurement accuracy of the first sensor corresponding to the first sensor data

603

Train a machine learning model using data input including first metrology data (and target output including the measurement accuracy of the first sensor to generate a trained machine learning model configured to generate outputs that include an indication of an accuracy level of a sensor associated with the metrology data

END

START

611

Receive current data (metrology data) associated with cell growth of a current cell culture

612

Provide the current data to a trained machine learning model

613

Obtain, from the trained machine learning model, one or more outputs indicative of a sensor measurement accuracy of a sensor associated with the current data

614

Determine a measurement accuracy of the sensor to meet a threshold criterion

END

FIG. 6B

MULTI-LEVEL MACHINE LEARNING FOR PREDICTIVE AND PRESCRIPTIVE APPLICATIONS

TECHNICAL FIELD

The instant specification generally relates to multi-level machine learning. More specifically, the instant specification relates to identifying prescriptive actions to alter target product formation yields of a cell culture.

BACKGROUND

Cell culture is the process by which cells are grown under controlled conditions, generally outside their natural environment. After the cells of interest have been isolated from living tissue, the cells can subsequently be maintained under carefully controlled conditions. These conditions vary for each cell type, but generally consist of a suitable vessel with a substrate or medium that supplies the essential nutrients (e.g., amino acids, carbohydrates, vitamins, minerals), growth factors, hormone, and gases (e.g., $CO_2$, $O_2$), and regulates the physio-chemical environment (pH buffer, osmotic pressure, temperature). Some cells require a surface or an artificial substrate (e.g., adherent or monolayer culture) whereas others can be grown free floating in a culture medium (e.g., suspension culture).

SUMMARY

A method and a system for identifying prescriptive action to alter a target product output yield of a cell culture of a cell growth system. In some embodiments, the method can include receiving cell growth data with a current cell culture of a cell growth system. The cell growth data includes a current cell count of the current cell culture and growth input parameter values indicative of a growth rate of the current cell culture. The method further includes identifying, using a first machine learning model, a prescriptive action to alter a yield of a target product of the current cell culture based on the cell growth data. The prescriptive action modifies a metabolism rate of the current cell culture. The method further includes performing at least one of displaying the identified prescriptive on a graphical user interface (GUI) and/or causing the cell growth system to perform the identified prescriptive action.

In some embodiments, a method for training a machine learning model to identify a prescriptive action to be performed by a cell growth system to modify an overall cell metabolism of a cell culture is performed. The method includes generating training data for the machine learning model. Generating the training data may include identifying a first training input having first cell growth data that includes a first cell count and one or more first growth input parameter values indicative of a first growth rate of a first cell culture. Generating the training data may further include identifying a first target output for the first training input. The first target output may include a first prescriptive action that alters a first yield of a target product of the first cell culture. The first prescriptive action can modify a first metabolism rate of the first cell culture. The method may further include providing the training data to train the machine learning model on (i) a set of training inputs comprising the first training input; and (ii) a set of target outputs comprising the first target output. The trained machine learning model may receive a new input having new cell growth data including a new cell count and one or more new growth input parameter values indicative of a new growth rate of a new cell culture and produce a new output based on the new input. The new output may indicate a new prescriptive action that alters a new yield of the target product of the new cell culture. The new prescriptive action can modify a new metabolism rate of the new cell culture.

BRIEF DESCRIPTION OF THE DRAWINGS

Aspects and implementations of the present disclosure will be understood more fully from the detailed description given below and from the accompanying drawings, which are intended to illustrate aspects and implementations by way of example and not limitation.

FIG. 4 depicts a flow diagram of one example method for processing growth data to identify prescription action associated with altering a target product yield of a cell culture using a trained machine learning model, in accordance with some implementation of the present disclosure.

FIG. 6A-B depict flow diagrams of methods 600A-B associated with determining measurement accuracy of sensor, according to certain embodiments

DETAILED DESCRIPTION

Figure 1:
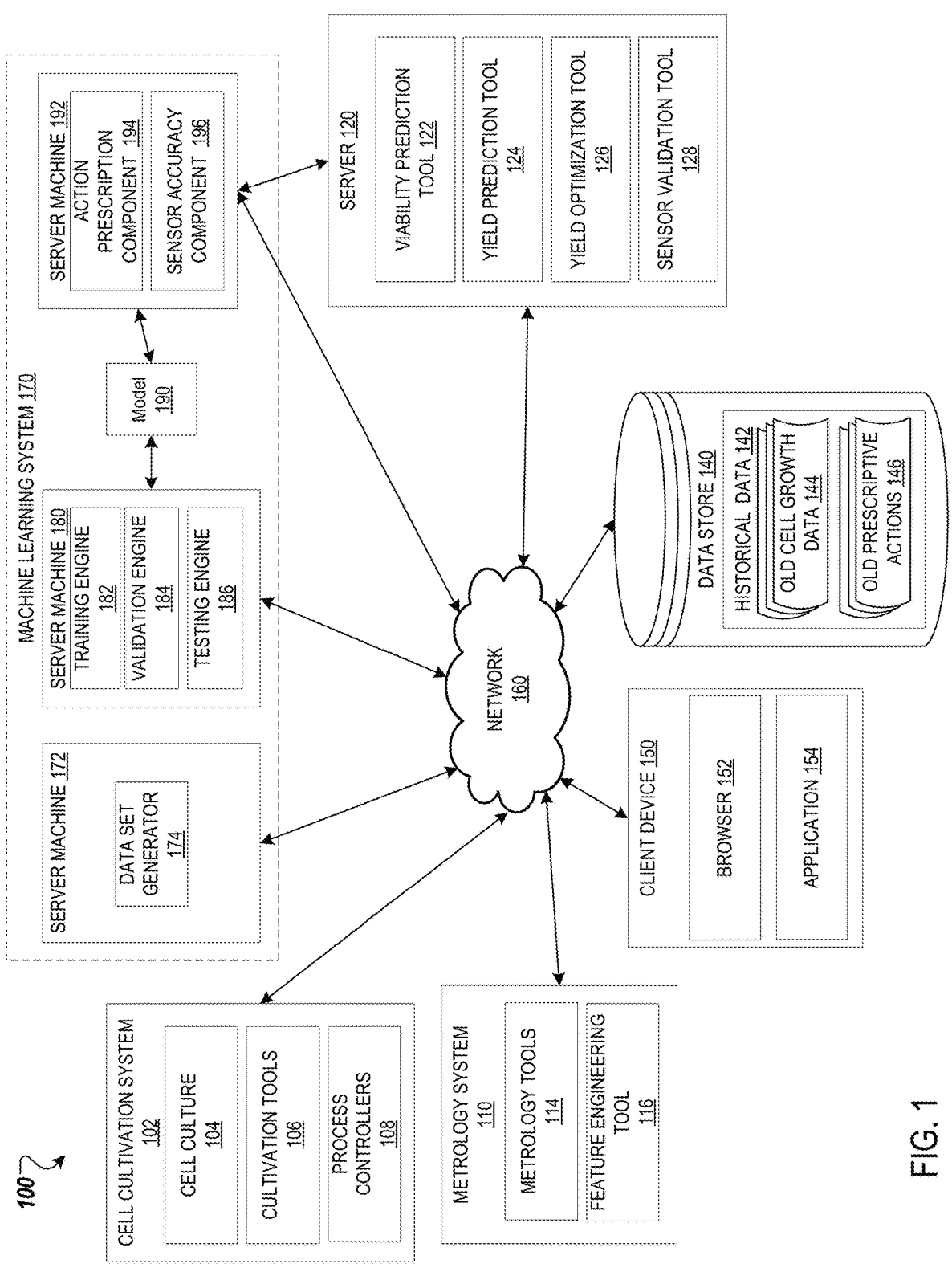
FIG. 1 is a block diagram illustrating an exemplary system architecture in which implementations of the disclosure may operate.

A cell growth system may involve a variety of growth input parameters or process parameters that are used to control a growth process of a cell culture. For example, growth input parameters can include a feeding schedule (e.g., flow rate of a nutrient such as glucose), oxygen flow rate, air flow rate, agitation parameters (e.g., mixing, stirring, heating, pressurizing, pH buffer, etc.), and so on. These parameters can be managed through process controllers (e.g., feeding valve, oxygen intake, agitation devices, etc.). The growth input parameters at various combinations with various contribution levels can affect a growth rate (e.g., cell count, cell density, target product formation, etc.) of a cell culture. For example, growth input factors can alter an environment in which a cell culture is growing. For example, providing nutrient to the environment can enable metabolism by the cells. In another example, altering the pressure, temperature, and/or acidity of the environment can modify the environment to be more conducive to cell growth. In order for process controllers to perform their function effectively, quick and accurate turnaround and processing of cell growth data (e.g., data indicative of environmental conditions of the growing environment) is often needed.

A cell growth system often uses a wide range of sensors to measure a variety of environmental parameters to monitor the growing conditions of the growth environment. Various amounts of growth data is collected throughout the growth process of a cell culture. The environment data can be used to coordinate prescriptive actions to be taken by the process controllers to alter growth input parameters and modify the growth environment. For example, a sensor can measure that the environment is getting too hot and thus should reduce temperature. However, some process parameters, such as cell density, cell count, target product yield, and the like are often difficult to measure. For example, methods for measuring process parameters are commonly measured offline or through a process analytical technology (PAT) sensor. PAT sensors are commonly used as a mechanism to design, analyze, and control pharmaceutical manufacturing processes through the measurement of critical process parameters (CPPs) (e.g., nutrient density) which can affect critical quality attributes (CQA) (e.g., cell density, cell count, target product yield, etc.). Thus, there is a need to be able to identify a good operating sensor (e.g. dependable measurement accuracy) for process control strategies as well as sensor health for maintenance. Inferring critical parameter using robust mechanistic features combined with reliable PAT sensor information and existing process data into advanced machine learning algorithms can be used for prediction/optimization of the cell growth system.

Aspects and implementations of the present disclosure address these and other shortcoming of the existing technology by providing integration of existing PAT sensor into machine learning algorithms for selection of ideal controlling sensors used in feedback process control. For example, a linear exponential regression can be used on a novel mechanistic feature to predict viable cell density. In another example, some embodiments provide PAT sensor data into staged machine learning algorithms to predict and/or optimize cell growth processes by prescribing actions and feedback control capability to adapt to process variation in advanced machine learning control strategies. For example, predicting and/or optimizing and target output formation of a cell culture.

In an exemplary embodiment, a processing system can receive cell growth data associated with a current cell culture of a cell system. The cell growth data can comprise a current cell count of the current cell culture. The growth input parameters values can be indicative of a growth rate of the current cell culture. The processing system can identify, using a machine learning model (or through various stages or multiple machine learning models), a prescriptive action that modifies a metabolism rate of the current cell culture based on the cell growth data. The processing system can display the identified prescriptive action on a graphical user interface (GUI). Alternatively or additionally, the processing system can cause the cell growth system to perform the identified prescriptive action.

Aspects of the present disclosure provide various technological advantages and improvements over conventional systems. As previously outlined, methods for measuring CPPs can be difficult, lack reliability, and/or generally be inefficient. In some embodiments, a "virtual" sensor can replace convention sensors that require manual sample measurement and off-line analysis. In some embodiments, a more consistent understanding of sensor health and control probe selection can avoid poor process performance and possible batch deviations (e.g., between different culture of the same growth process). In some embodiments, processing system and methodology as described herein provide early fault detection for PAT sensors and/or predictive maintenance capabilities. In some embodiments, processing systems and methodology provide for early prediction of batch performance and can measure target product yield mid-run as opposed to offline yield measurements as conventionally performed. In some embodiments, processing systems and methodology provides for advanced ML optimization of process step strategies (e.g., feed strategies) within (e.g. while the growth system is online) to maximize yield through prescriptive actions.

FIG. 1 is a block diagram illustrating an exemplary system architecture 100 in which implementations of the disclosure may operate. As shown in FIG. 1, system architecture 100 includes a cell cultivation system 102, a metrology system 110, a client device 150, a data store 140, a server 120, and a machine learning system 170. The machine learning system 170 may be part of the server 120. In some embodiments, one or more components of the machine learning system 170 may be fully or partially integrated into client device 112. The cell cultivation system 102, the metrology system 110, the client device 150, the data store 140, the server 120, and the machine learning system 170 can each be hosted by one or more computing devices including server computers, desktop computers, laptop computers, tablet computers, notebook computers, personal digital assistants (PDAs), mobile communication devices, cell phones, hand-held computers, or similar computing devices.

The cell cultivation system 102, the metrology system 110, client device 150, data store 140, server 120, and machine learning system 170 may be coupled to each other via a network 160 (e.g., for performing methodology described herein). In some embodiments, network 160 is a private network that provides each element of system architecture 100 with access to each other and other privately available computing devices. Network 160 may include one or more wide area networks (WANs), local area networks (LANs), wired network (e.g., Ethernet network), wireless networks (e.g., an 802.11 network or a Wi-Fi network), cellular network (e.g., a Long Term Evolution (LTE) network), routers, hubs, switches, server computers, and/or any combination thereof. Alternatively or additionally, any of the elements of the system architecture 100 can be integrated together or otherwise coupled without the use of network 160.

The client device 150 may be or include any personal computers (PCs), laptops, mobile phones, tablet computers, netbook computers, network connected televisions ("smart TV"), network-connected media players (e.g., Blue-ray player), a set-top-box, over-the-top (OOT) streaming devices, operator boxes, etc. The client device 150 may include a browser 152, an application 154, and/or other tools as described and performed by other systems of the system architecture 100. In some embodiments, the client device 150 may be capable of accessing the cell cultivation system 102, the metrology system 110, the data store 140, server 120, and/or machine learning system 170 and communicating (e.g., transmitting and/or receiving) indication of prescriptive actions, growth parameter data, and/or inputs and outputs of various process tools (e.g., metrology tool 114, viability prediction tool 122, yield prediction tool 124, yield optimization tool 126, sensor validation tool 128, and/or model 190) at various stages processing of the system architecture 100, as described herein.

As shown in FIG. 1, cell cultivation system 102 includes a cell culture 104 and cultivation tools 106 that manage growth input parameters and environmental conditions to facilitate a growing environment for the cell culture 104 within the cell cultivation system 102. The cell system further includes process controllers 108 that coordinate actions to be performed by the cultivation tools 106. The coordinated action may be associated with altering a growth outcome of the cell culture (e.g., increased viable cell density, increased cell growth, increased target product formation, etc.) Process controllers 108 may receive input from other features (e.g., machine learning system 170, server 120 metrology system 110, etc.) of system architecture 100 to manage and control a cell growth process (e.g., to facilitate a specific growth outcome).

Cultivation tools 106 can include various mechanistic devices that alter various input and/or outputs as well as environmental condition of a growth environment housing the cell culture 104. For example, cultivation tools 106 can include, for example, a feeding pump, an air control valve or pump, an aerator (e.g., a submerged sparge aerator), a thermal jacket, feeding valves (e.g., nutrient valves), effluent valve, and an agitation system (e.g., mixing or stirring devices, hearing system, pressure system, pH buffers, etc.), to name a few.

Process controllers 108 can include devices designed to manage and coordinate the actions of cultivation tools 106. In some embodiments, process controllers 108 are associated with a growth recipe or growth process instructions that when applied in a designed manner result in a desired cell growth outcome of cell culture 104. For example, a process recipe may be associated with growing the cell culture to produce a target product outcome (e.g., a protein, a chemical composition, cell mutations, etc.)

As shown in FIG. 1 metrology system 110 includes metrology tools 114 and data engineering tools 116. Metrology tools 114 can include a variety of sensors to measure and detect parameters within the cell cultivation system 102. For example, PAT sensor can be used to measure a variety of critical process parameters (CCPs) (e.g., cell count, cell density, target product output) associated with a process recipe and/or action performed by process controllers 108. In another example, the variety of sensors can measure conditions of a growing environment of the cell culture 104. For example, parameters such as temperature, pressure, acidity, density, and the like can be measured in association with the growth environment.

Feature engineering tool 116 may include process methodology to extract features and/or generate synthetic/engineered data associated with data measured by metrology tools 114. In some embodiments, feature engineering tool 116 can identify correlations, patterns, and/or abnormalities of metrology or process performance data. For example, feature engineering tool 116 may perform a feature extraction where data engineering tool 161 uses combinations of measured data to determine whether a criterion is satisfied. For example, feature engineering tool 116 can analyze multiple data points of an associated parameter (e.g., temperature) to determine whether rapid changes occurred over a growth stage (e.g., cell division) of a growth cycle of the cell culture.

In some embodiments, feature engineering tool 116 can perform one or more of a process control analysis, univariate limit violation analysis, or a multivariate limit violation analysis on metrology data (e.g., obtained by metrology tools 114). For example, feature engineering tool 116 can perform statistical process control (SPC) by employing statistics based methodology to monitor and control process controllers 108. For example, SPC can promote efficiency and accuracy of a growth process (e.g., growth recipe) of the cell cultivation system (e.g., by identifying data points that falls within and/or outside control limits).

In some embodiments, the feature engineering tool 116 can perform univariate and multivariate limit violation analysis to generate various amounts synthetic data (e.g., combinations of one or more engineered data points) indicative of various combinations, correlations, and/or outliers of metrology data. For example, feature engineering tool 116 may include an SPC database and/or SPC charts associated with metrology data obtained through metrology tools 114.

In some embodiments, a cell culture can be measured throughout a growth period. In some embodiments, increased amounts of metrology data is taken during predetermined growth stages. For example, during a key growth stage or process (e.g., cell division stages), additional sensors can be activated and/or currently activated sensor may take additional data. In some embodiments, process controllers 108 may trigger measurement by metrology tools 114 based on operations to be performed by cultivation tools 106. For example, process controllers 108 can trigger activation of one or more sensors (e.g. of metrology tools 114) responsive to actuation of a feeding valve (e.g. of cultivation tools 106).

In some embodiments, the extracted features, generated synthetic/engineered data, and statistical analysis can be used in association with machine learning system 170 (e.g., to train, validate, and/or test machine learning model 190). Additionally and/or alternatively, feature engineering tool 116 can output data to server 120 to be used by any of viability prediction tool 122, yield prediction tool 124, yield optimization tool 126, and/or sensor validation tool 128.

Data store 140 may be a memory (e.g., random access memory), a drive (e.g., a hard drive, a flash drive), a database system, or another type of component or device capable of storing data. Data store 140 may store one or more historical data 142 including old cell growth data 144 and/or old prescriptive actions 146 of previous cell cultures cultivated in a similar cell cultivation system (e.g., cell cultivation system 102), growth input parameters, and/or growth process recipes. In some embodiments, the historical data 142 may be used to train, validate, and/or test a machine learning model 190 of machine learning system 170 (See e.g., FIG. 5 for exemplary methodology).

Server 120 may include one or more computing devices such as a rackmount server, a router computer, a server computer, a personal computer, a mainframe computer, a laptop computer, a tablet computer, a desktop computer, etc. The server 120 can include a viability prediction tool 122, a yield prediction tool 124, yield optimization tool 126, and a sensor validation tool 128.

The viability prediction tool 122 receives metrology data from metrology system 110 and determines a predicted viable cell density of the cell culture 104. In some embodiments, the viability prediction tool receives raw sensor data from metrology tool 114, in other embodiments, raw sensor data is combined with synthetic data engineered from feature engineering tool 116. The viability prediction tool 122 may include a growth prediction model (e.g., mechanistic model 210 or statistical model 212 of FIG. 2 or graph 300 of growth prediction model of FIG. 4). The growth prediction model may be generated using historical data 142. For example, the viability prediction tool can apply a regression (e.g., linear exponential regression, least square regression, etc.) on the historical data 142 to generate the prediction model. Generation of the cell prediction model will be discussed further in associated with FIGS. 2 and 5. In some embodiments, the viability prediction tool may use a machine learning model to receive metrology data and output a predicted viable cell density of the cell culture 104.

The yield prediction tool 124 determines a predicted yield of a target product formation of the cell culture 104. As previously described, the target product formation may include a measurable product formed by the cell as a result of cultivation. For examples, various proteins are a commonly formed by cells during a cell growth process. In some embodiments, the yield prediction tool includes a machine learning model that uses metrology data (e.g., sensor data (e.g., by metrology tools 114), synthetic and/or engineered data (e.g., from feature engineering tool 116, general process parameter values, growth input parameter values, and/or general cell growth data) and predicts a future yield of the target product formation. As will be discussed later, the yield prediction tool 124 can use machine learning system 170 to train the machine learning model. For example, the machine learning model associated with the yield prediction too may be trained using supervised learning with the historical data 142. As will be discussed further in later embodiments, the machine learning model may include a decision tree such a random forest that evaluates features (e.g., variable, factors, and/or parameters associated with the cell cultivation system 102 and growth process) to predict a future yield of a product formation of the cell culture 104.

The yield optimization tool 126 coordinates with the yield prediction tool to suggest a prescriptive action (e.g., a change in the growth process, operation of cultivation tools, adjusting to a growth environment, etc.) that when, performed, alters the yield of a target product formation. For example, the prescriptive action may modify an overall cell metabolism of the cell culture 104 by prescribing an optimal feeding schedule to be performed by the cell cultivation system. The optimal feeding schedule facilitates cell growth resulting in an increase target product formation by the cells. As will be discussed further in later embodiments, the yield optimization tool may include a machine learning model or be a part of the machine learning model associated with the yield prediction tool 124. For example, the yield optimization tool may run multiple actions that could be applied to the cell cultivation system against the yield prediction tool (e.g., as input to a machine learning model) to receive multiple yield predictions that can be used to determine an optimized action to be taken by the cell cultivation system.

The sensor validation tool 128 receives metrology data corresponding to various metrology tools 114 (e.g., PAT sensors) and determines a confidence level of each metrology tool. For example, two PAT sensors may be measuring CCPs of the cell cultivation system. As previously mentioned, PAT sensor often suffer from inaccuracy (e.g., from measurement drift and variability). The sensor validation tool 128 identifies a confidence level associated with each sensor and recommends one as having the highest confidence level. In some embodiments, the sensor validation tool 128 uses a trained machine learning model to identify the confidence level for each sensor. As will be discussed further in other embodiments, the machine learning model may include a model trained using unsupervised training method such as principal component analysis or using a feature support vector. (e.g., see FIGS. 6A-B for exemplary methodology)

As previously described, some embodiments of the viability prediction tool 122, yield prediction tool 124, yield optimization tool 126, and/or sensor validation tool 128 may perform their described methodology using a machine learning model. The associated machine learning models may be generated (e.g., trained, validated, and/or tested) using machine learning system 170. The following exemplary description of machine learning system 170 will be described in the context using machine learning system 170 to generate a machine learning model 190 associated with optimizing the yield prediction tool (e.g., include aspects of both the yield prediction tool and the yield optimization tool). However, it should be noted that this description is purely exemplary. Analogous processing hierarchy and methodology can be used in the generation and execution of machine learning models associated with the viability prediction tool 122, the yield prediction tool 124, the yield optimization tool 126, and/or the sensor validation tool 128 individually and/or in combination with each other, as will be discussed further in association with other embodiments.

The machine learning system 170 may include one or more computing devices such as a rackmount server, a router computer, a server computer, a personal computer, a mainframe computer, a laptop computer, a tablet computer, a desktop computer, etc. The machine learning system 170 may include an action prescription component 194. In some embodiments, the action prescription component 194 may use historical data 142 to prescribe an action that when applied to the cell cultivation system alters a yield of a target product formation by cell culture 104. In some embodiments, the action prescription component 194 may use a trained machine learning model 190 to prescribe an action to be performed by the cell cultivation system 102 to alter a yield of a target product formation. The trained machine learning model 190 may use historical data to prescribe the actions to be performed by the cell cultivation system 102.

In some embodiments, the machine learning system 170 further includes server machine 172 and server machine 180. The server machine 172 and 180 may be one or more computing devices (such as a rackmount server, a router computer, a server computer, a personal computer, a mainframe computer, a laptop computer, a tablet computer, a desktop computer, etc.), data stores (e.g., hard disks, memories databases), networks, software components, or hardware components.

Server machine 172 may include a data set generator 174 that is capable of generating data sets (e.g., a set of data inputs and a set of target outputs) to train, validate, or test a machine learning model. The data set generator 174 may partition the historical data 142 into a training set (e.g., sixty percent of the historical data, or any other portion of the historical data), a validating set (e.g., twenty percent of the historical data, or some other portion of the historical data), and a testing set (e.g., twenty percent of the historical data). In some embodiments, the action prescription component 194 generates multiple sets of training data. For example, one or more sets of training data may include each of the data sets (e.g., a training set, a validation set, and a testing set).

Server machine 180 includes a training engine 182, a validation engine 184, and a testing engine 186. The training engine 182 may be capable of training a machine learning model 190 using one or more old cell growth data 144 and old prescriptive action 146 of the historical data 142 (of the data store 140). In some embodiments, the machine learning model 190 may be trained using one or more outputs of the feature engineering tool 116, the sensor validation tool 128, the yield optimization tool 126, yield prediction tool 124, and/or viability prediction tool 122. For example, the machine learning 190 may be a hybrid machine learning model using cell growth data and/or mechanistic features such as a feature extraction, mechanistic modeling and/or statistical modeling (e.g., using feature engineering tool 116, discussed further is association with feature extractor 208, mechanistic model 210, and/or statistical model 212 in FIG. 2) The training engine 182 may generate multiple trained machine learning models 190, where each trained machine learning model 190 corresponds to a distinct set of features of each training set.

The validation engine 184 may determine an accuracy of each of the trained machine learning models 190 based on a corresponding set of features of each training set. The validation engine 184 may discard trained machine learning models 190 that have an accuracy that does not meet a threshold accuracy. The testing engine 186 may determine a trained machine learning model 190 that has the highest accuracy of all of the trained machine learning models based on the testing (and, optionally, validation) sets.

In some embodiments, the training data is provided to train the machine learning model 190 such that the trained machine learning model is to receive a new input having new cell growth data comprising a new cell count and one or more new growth input parameter values indicative of a new growth rate of a new cell culture and to produce a new output based on the new input, the new output indicating a new prescriptive action that alters a new yield of the target product of the new cell culture, wherein the new prescriptive action modifies a new metabolism rate of the new cell culture.

The machine learning model 190 may refer to the model that is created by the training engine 182 using a training set that includes data inputs and corresponding target output (historical results of cell cultures under parameters associated with the target inputs). Patterns in the data sets can be found that map the data input to the target output (e.g. identifying connections between portions of the cell growth data and resulting yield of the target product formation), and the machine learning model 190 is provided mappings that captures these patterns. The machine learning model 190 may use one or more of logistic regression, syntax analysis, decision tree, or support vector machine (SVM). The machine learning may be composed of a single level of linear of non-linear operations (e.g., SVM) and/or may be a neural network.

Function identification component 194 may provide current data (e.g., current cell growth data associated with the current cell culture 104) as input to trained machine learning model 190 and may run trained machine learning model 190 on the input to obtain one or more outputs including a prescriptive action to be performed by the cell cultivation system to alter the yield of a target product formation of the cell culture 104. For example, to optimize (e.g., maximize the yield of the target product formation). The action prescription component 194 may be capable of identifying confidence data from the output that indicates a level of confidence that one or more prescriptive actions will alter the yield of the target product formation. For example, the prescriptive action may modify the overall metabolism of the cell culture to increase the yield of the target product formation.

The confidence data may include or indicate a level of confidence of one or more prescriptive actions that when performed by the cull cultivation system 102 will result in an altered yield (e.g. increased or maximized) of the target product formation. In one non-limiting example, the level of confidence is a real number between 0 and 1 inclusive, where 0 indicates no confidence of the one or more prescriptive actions and 1 represents absolute confidence in the prescriptive action.

For purpose of illustration, rather than limitation, aspects of the disclosure describe the training of a machine learning model and use of a trained learning model using information pertaining to historical data 142. In other implementation, a heuristic model or rule-based model is used to determine a prescriptive action.

In some embodiments, the functions of client devices 112, server 120, data store 140, and machine learning system 170 may be provided by a fewer number of machines than shown in FIG. 1. For example, in some embodiments server machines 172 and 180 may be integrated into a single machine, while in some other embodiments server machines 172, 180, and 192 may be integrated into a single machine. In some embodiments, the machine learning system 170 may be fully or partially provided by server 120.

In general, functions described in one embodiment as being performed by client device 150, data store 140, metrology system 110, cell cultivation system 102, and machine learning system 170 can also be performed on server 120 in other embodiments, if appropriate. In addition, the functionality attributed to a particular component can be performed by different or multiple components operating together.

In embodiments, a "user" may be represented as a single individual. However, other embodiments of the disclosure encompass a "user" being an entity controlled by multiple users and/or an automated source. For example, a set of individual users federated as a group of administrators may be considered a "user."

Figure 2:
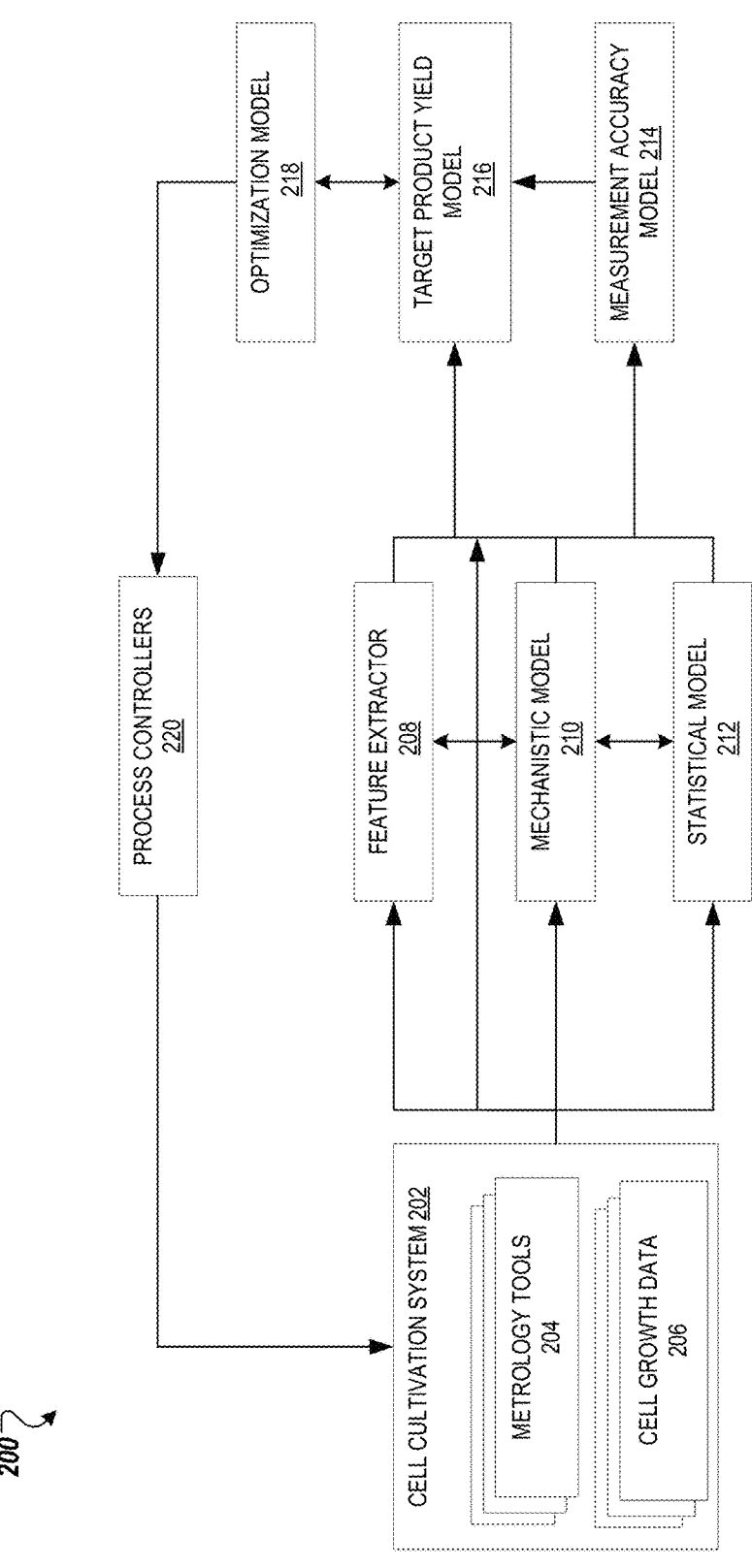
FIG. 2 is a block diagram illustrates a multi-level machine learning system architecture in which implementations of the disclosure may operate.

FIG. 2 is a block diagram that illustrates a multi-level machine learning system 200 in which implementations of the disclosure may operate. The multi-level machine learning system 200 includes a cell cultivation (e.g., cell cultivation system 102 of FIG. 1). The cell cultivation system may include metrology tools 204 and cell growth data 206 (e.g., acquired using metrology tools 204). The metrology tools can include PAT sensors, process control sensors, and the like (e.g., a bio-capacitance sensor). The cell cultivation system cultivates a cell culture in a growth environment. The cell growth data 206 can include data indicative of environmental conditions of the growth environment. For example, metrology tools 204 can measure and monitor parameters such as temperature, pressure, acidity, capacitance, to name a few. Additionally the cell growth data may include data indicative of growth input factors such feeding schedule (e.g., when and how much nutrient is being added to the system), input flow (e.g., oxygen flow rate, airflow rate, to the system), agitation being applied (e.g., a stirring rate, or a mixing rate of the cells). Additionally, the cell cultivation system may further include offline measurement techniques such a measuring cell count, density, and target product formation. Various type and various combinations of cell growth data 206 can be obtained by metrology tools 204 and aggregated together for data processing.

In some embodiments, cell growth data 206 is processed by feature extractor 208. The feature extractor 208 can receive cell growth data (e.g., raw sensor data) and generate synthetic data associated with various combinations, correlations, artificial parameters. The feature extractor 208 can dimensionality reduce the raw sensor data into groups or features. For example, the feature extractor may generate features that include the rate of change of a parameter value and/or a collection of parameters value. In some embodiments, feature extractor 208 performs any of partial least squares analysis, principal component analysis, multifactor dimensionality reduction, nonlinear dimensionality reduction, and/or any combination thereof. In some embodiments, the feature extractor is designed for edge detection of the cell growth data. For example, the feature extractor includes methodology that aims at identifying data points that change sharply and/or that have discontinuities. For example, the slope of a capacitance measurement of a bio capacitance sensor.

In some embodiments, cell growth data 206 is processed using a mechanistic model 210. The mechanistic model 210 examines the workings of individual data points of the cell growth data 206 and the manner to which the individual data points are coupled to determine a physical/mechanistic representation of the data coupling. In some embodiments, the mechanistic model 210 may include processing the data to determine a prediction of the cell cultivation system 202. For example, the mechanistic model 210 may process the cell growth data 206 to determine a viable cell density prediction of a cell culture of the cull cultivation system 202. The mechanistic model 210 may be generated using historical data and later used on current data to determine a prediction.

In some embodiments, the mechanistic model 210 is determined using data regression analysis. For example, any of linear regression, nonlinear regression, exponential regression, least square regression, and/or any combination thereof can be used to generate mechanistic model 210. In some embodiments, the mechanistic model identifies multiple physical dependencies between the data and generates various predicted values associated with the cell growth data 206 and the physical dependencies. In some embodiments, the model can be used to output predictions (e.g., a future or expected value and/or a current parameter value difficult to obtain), updated data values (e.g., calibrate data points), and/or relationships between the individual data points (e.g., a regression equation and/or trend line).

In some embodiments, cell growth data is processed using statistical model 212. Statistical model 212 may be used to process the data based on statistical operations to validate, predict, and/or transform the cell growth data 206. In some embodiments, the statistical model 212 is generated using statistical process control (SPC) analysis to determine control limits for data and identify data as being more or less dependable based on those control limits. In some embodiments, the statistical model 212 is associated with univariate and/or multivariate data analysis. For example, various parameter can be analyzed using the statistical model 212 to determine patterns and correlations through statistical processes (e.g., range, minimum, maximum, quartiles, variance, standard deviation, and so on). In another example, relationships between multiple variables can be ascertained using regression analysis, path analysis, factor analysis, multivariate statistical process control (MCSPC) and/or multivariate analysis of variance (MANOVA).

In some embodiments, statistical model 212 incorporates a first analysis of variance (ANOVA) calculated on each growth step and parameter value to identify variation within and across the various cell cultures (e.g., historical data) associated with the same growth process (e.g. growth recipe, target output) to compare data cell culture to cell culture. In some embodiments, a second ANOVA is calculated within and across an individual cell culture to compare various parameter values, conditions, other data within an individual cell culture. In some embodiments, a third ANOVA is calculated within and across the entire cell growth data (e.g., a combination of the first ANOVA and the second ANOVA). The first ANOVA, the second ANOVA, and the third ANOVA may then be used to generate a sample pattern for cell growth of a current cell culture.

In some embodiments, one or more of feature extractor 208, mechanistic model 210, and/or statistical model 212 are used to generate input for measurement accuracy model 214.

As discussed further in other embodiments, the measurement accuracy model 214 receives input data (e.g., raw sensor data, synthetic data, outputs of other models, etc.) to determine a measurement accuracy of one or more metrology tools 204 associated with the cell growth data 206 (e.g., acquisition, processing, calibrating, etc.) In some embodiments, the measurement accuracy model may incorporate a machine learning model (e.g., trained using method 600A and/or implemented using method 600B). In some embodiments, the measurement accuracy model incorporates aspects or features of feature extractor 208, mechanistic model 210, and/or statistical model 212. For example, measurement accuracy model 214 may determine an accuracy of an individual sensor using SPC. In another example, measurement accuracy model 214 may receive as output an indication of sensor accuracy (e.g. a measurement tolerance window).

In some embodiments, the measurement accuracy model 214 acts as a data filter, removing data that is associated with a metrology tool that is below a threshold confidence level associated with measurement accuracy. In another embodiment, the measurement accuracy model 214 assigns a weight to individual data based on the confidence level of a metrology tool used in associated with that individual data.

In some embodiments, raw cell growth data 206 and/or outputs of one or more of feature extractor 208, mechanistic model 210, statistical model 212, and/or measurement accuracy model 214 are used as inputs to a target product yield model 216. As discussed further in other embodiments, the target product yield model 216 receives input and determines a predicted future yield of a target product formation of a cell culture associated with cell cultivation system 202. The target product yield model may incorporate use of a machine learning model (e.g., trained using method 500 of FIG. 5, implemented using method 400 of FIG. 4, using processing architecture of machine learning system 170 of FIG. 1)

In some embodiments, the target product yield model 216 is combined with and/or is associated with an optimization model 218. The optimization model 218 may be a trained model for optimization hyper parameters associated with the target product yield model 216. In some embodiments, the optimization model is generated and/or implemented using an instance of the Broyden-Fletcher-Goldfarb-Shanno (BFGS) algorithm, a conjugate gradient (CG) algorithm, an instance of the Nelder-Mead algorithm, and/or a model predictive control (MPC) algorithm.

In some embodiments, the optimization model 218 may receive cell growth data 206 and use the target product yield model 216 to predict a target product formation yield. The optimization model may alter the data to predict effects of the target product formation from various changes to the cell data to determine a prescriptive action to be performed by process controllers 220. The prescriptive action can be applied by process controllers 220 to alter a target production formation yield of a cell culture associated with the cell cultivation system 202. For example, the prescriptive action may result in modifying the metabolism rate of cells of the cell culture (e.g., by altering a feeding schedule).

Process controllers 220 may provide instructions to the cell cultivation system 202 in carrying out a growth process on a cell culture. The process controllers 220 may provide instructions associated with prescriptive actions identified by the optimization model 218 and/or the target product yield model 216. For example, process controller may provide instruction such as start feeding in 1 hour, increase temperature of growth environment, increase stirring/mixing speed of cell culture, and so on.

Figure 3:
FIG. 3 depicts a graph illustrating a growth prediction model, in accordance with some implementations of the present disclosure.

FIG. 3 depicts a graph 300 illustrating a growth prediction model, in accordance with some implementations of the present disclosure. Graph 300 depicts data as received and process by a growth model (e.g., any of feature extractor 208, mechanistic model 210, statistical model 212, measurement accuracy model 214, target product yield model 216, and/or optimization model 218 of FIG. 2) Data series 302 represents an initiation (e.g., start time) of feeding a cell culture. Data series 304 includes sensor data measured by a first sensor (e.g. a first bio capacitance sensor). Data series 306 includes sensor data measured by a second sensor (e.g. a second bio capacitance sensor). Data series 310 includes data associated with an off-line metrology cell-count measurement. Data series 308 represents a cell count prediction determined using data processing techniques described herein. In some embodiments, a prescriptive action is identified and acted upon by the cell cultivation system. For example, the initiation time of feed (show as the bend in 302) increases the cell growth (shown as increases of step size of data series 310).

FIGS. 4-7 depict flow diagrams illustrating example methods 400-700 related to training and/or using machine learning models in association with cell growth data, in accordance with some implementation of the present disclosure. For simplicity of explanation, methods 400-700 are depicted and described as a series of acts. However, acts in accordance with this disclosure can occur in various orders and/or concurrently and with other acts not presented and described herein. Furthermore, not all illustrated acts may be performed to implement the methods 400-700 in accordance with the disclosed subject matter. In addition, those skilled in the art will understand and appreciate that methods 400-700 could alternatively be represented as a series of interrelated states via a state diagram or events.

FIG. 4 depicts a flow diagram of one example method for processing growth data to identify a prescription action associated with altering a target product yield of a cell culture using a trained machine learning model, in accordance with some implementation of the present disclosure. Method 400 is performed by processing logic that may comprise hardware (circuitry, dedicated logic, etc.), software (such as is run on a general purpose computer system or a dedicated machine) or any combination thereof. In one implementation, the method is performed using the server 120 and the trained machine learning model 190 of FIG. 1, while in some other implementations, one or more blocks of FIG. 4 may be performed by one or more other machines not depicted in the figures.

Method 400 may include receiving a cell growth data (e.g., associated with a cell cultivation system such as cell cultivation system of FIG. 1) and processing the cell growth data using a trained model such as trained machine learning model 190. The trained model may be configured to generate, based on cell growth data, one or more outputs indicating (i) a prescriptive action to alter a yield of a target product formation of the culture, and (ii) a level of confidence that the associated prescriptive action, when performed, alters the yield of the target product formation.

At block 401, cell growth data associated with a cell culture of a cell growth system (e.g., cell culture 104 of cell cultivation system 102 of FIG. 1) is identified. The cell growth data may include data indicative of growth input parameters such a measurable action being performed by cultivation tools (e.g., feeding or nutrient flow rate, oxygen flow rate, air flow rate, agitation rate (e.g., stirring or mixing), applied heat, applied pressure, etc.). The cell growth data my further include data measured by metrology tools (e.g., by metrology tools 114 of FIG. 1). For example, a PAT sensor can be used to measure critical process parameters (CPPs) and this PAT sensor data can be included in the received cell growth data.

In some embodiments, the cell growth data further includes synthetic data, or data engineered from raw sensor data. For example, as described in previous embodiments, various engineering tools can perform a feature extraction and/or create artificial and/or virtual parameter combinations. A feature extractor (e.g., feature engineering tool 116 of FIG. 1 or feature extractor 208 of FIG. 2) can create various features by performing variable analysis such as process control analysis, univariate limit violation analysis, and/or multivariate limit violation analysis on raw sensor data.

In some embodiments, the cell growth data includes outputs of other cell growth data models. For example, cell growth data may include a viable cell density prediction produce by a prediction model (e.g., using viability prediction tool 122, mechanistic model 210, and/or statistical model 212). In another embodiments, the cell growth data may be refined or filtered using a measurement accuracy model (e.g., measurement accuracy model 214 of FIG. 2 or sensor validation tool 128 of FIG. 1).

At block 402, the cell growth data is provided as input to the trained machine learning model, and at block 403, one or more outputs are obtained from the trained machine learning model. At block 404, confidence data is extracted from the output(s) obtained at block 404. In one implementation, the confidence data comprises, for each prescriptive action, a level of confidence that the associated predicted action alters a yield of a target product formation by the cell culture. In one example, the level of confidence is a real number between 0 and 1 inclusive. It should be noted that the level of confidence may not be a probability (for example, the sum of the confidences levels for the prescriptive actions may not equal 1).

At block 406, the confidence data is used to estimate one or more prescriptive actions that have a confidence level that satisfies a threshold condition. In one example, N prescriptive actions that have N highest levels of confidence may be identified as altering the target product formation of the cell culture. In another example, all prescriptive actions may be identified as altering the yield of the target product formation that have a level of confidence above a particular (e.g., predefined) threshold.

At block 406, the one or more identified prescriptive actions are provided for presentation on a graphical user interface (GUI) (e.g., for presentation to a user such as a system operator). In some embodiments, the prescriptive actions are presented to the user in rank order by confidence level. In some embodiments, the prescriptive actions are presented to the user with a visual indicator representing the confidence level associated with each prescriptive action. For example, one or more prescriptive actions with the highest confidence level may be depicted with first color (e.g., green or gold) and one or more prescriptive actions with a confidence level close to the threshold level may be depicted with a second color (e.g., yellow or silver). In some embodiments, the prescriptive actions may be placed in tiers or groups based on the associated confidence levels.

In some embodiments, alternatively or in addition to providing for present to a GUI, method 400 may include causing the prescriptive action to be applied by the cell cultivation system. In some embodiments after block 406, execution may continue back to 401 for processing of more cell growth data (e.g., updated sensor data, sensor data measured at a later time period, and/or cell growth data associated with the cell cultivation system after the identified prescriptive action has been applied).

Figure 5:
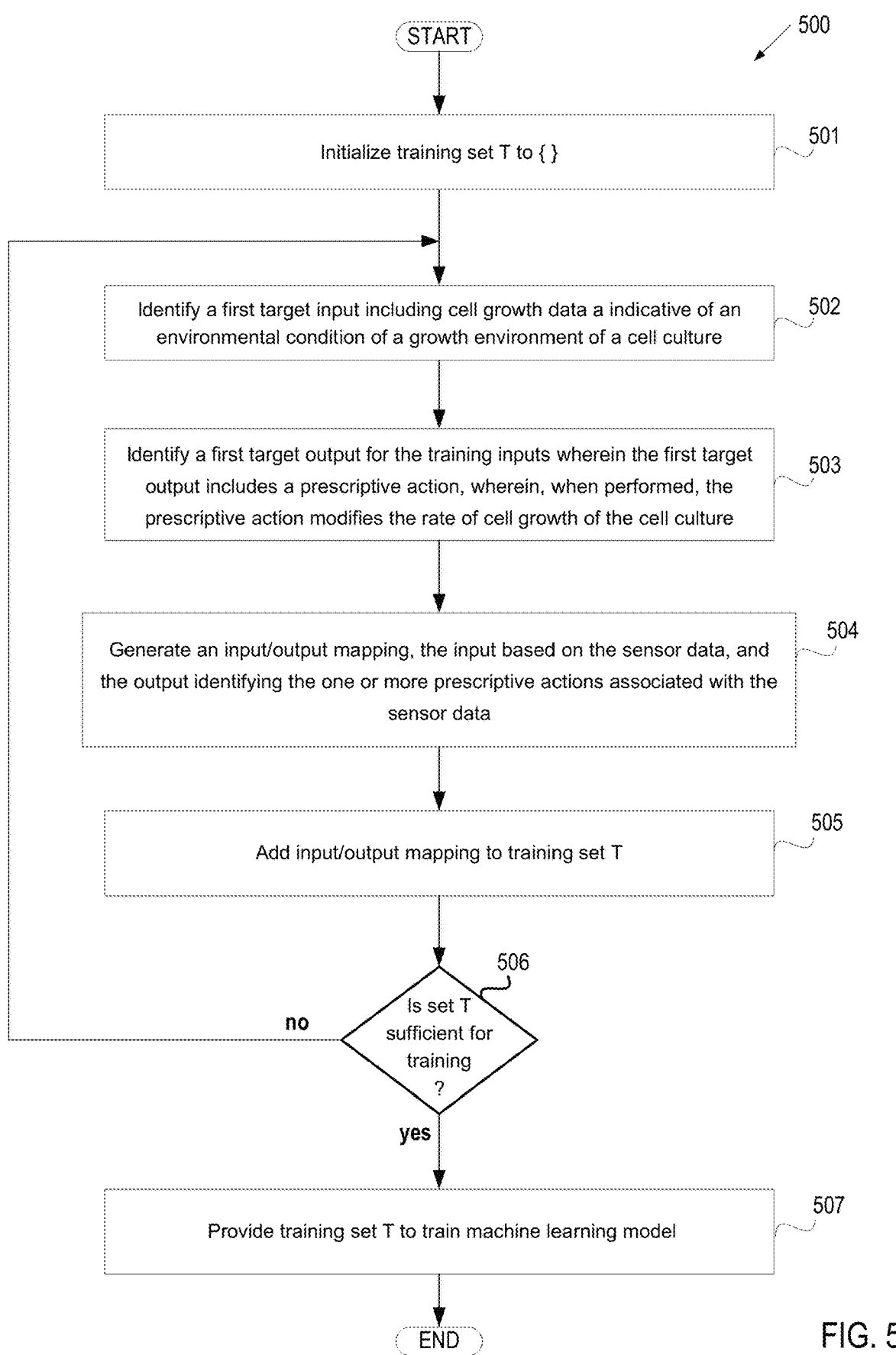
FIG. 5 is an exemplary illustration of a training phase of a machine learning system, in accordance with some implementation of the present disclosure.

FIG. 5 is an exemplary illustration of a training phase of a machine learning system, in accordance with some implementation of the present disclosure. Machine learning system 170 may use method 500 to at least one of train, validate, or test a machine learning model, in accordance with embodiments of the disclosure. In some embodiments, one or more operations of method 500 may be performed by data set generator 174 of server machine 172, as described with respect to FIG. 1. It may be noted that components described with respect to FIG. 1 may be used to illustrate aspects of FIG. 5.

Referring to FIG. 5, in some embodiments, at block 501 the processing logic implements method 500 by initializes a training set T to an empty set.

At block 502, processing logic identifies a first data input (e.g. first training input, first validating input) that includes a first cell growth (as described with respect to FIGS. 1-4). The first data input may include data indicative of an environmental condition of a growth environment of a previous cell culture. In some embodiments, the first data input may comprise any growth input parameter values (e.g., actions performed by cultivation tools such as feeding, providing oxygen and/or air, agitation, etc.). The first target input may be identified from the old cell growth data 144 of the historical data 142 (e.g., stored in the data store 140).

At block 503, processing logic identifies a first target output for one or more of the data inputs (e.g., first data input). The first target output provides an indication of a first prescriptive action that was applied to the previous cell cultivation and resulting yield of a target product formation by the previous cell culture. The first target input may be identified from the old cell growth data 144 of the historical data 142 (of data store 140).

At block 504, processing logic optionally generates mapping data that is indicative of an input/output mapping. The input/output mapping (or mapping data) may refer to the data input (e.g., one or more of the data inputs described herein), the target output for the data input (e.g. one or more of the data inputs described herein), the target output for the data (e.g. where the target output identifies an associated prescriptive action), and an association between the data input(s) and the target output.

At block 505, processing logic adds the mapping data generated at block 504 to data set T.

At block 506, processing logic branches based on whether the data set T is sufficient for at least one of training, validating, or testing machine learning model 190. If so ("yes" branch), execution proceeds to block 507, otherwise ("no" branch), execution continues back at block 502. It should be noted that in some embodiments, the sufficiency of data set T may be determined based simply on the number of input/output mappings in the data set, while in some other embodiments, the sufficiency of data set T may be determined based on one or more other criteria (e.g., a measure of diversity of the data examples, accuracy, etc.) in addition to, or instead of, the number of input/output mappings.

At block 507, processing logic provides data set T to train, validate, or test machine learning model 190. In some embodiments, data set T is a training set and is provided to training engine 182 of server machine 180 to perform the training. In some embodiments, data set T is a validation set and is provided to validation engine 184 of server machine

180 to perform the validating. In some embodiments, data set T is a testing set and is provided to testing engine 186 of server machine 180 to perform the testing. In the case of a neural network, for example, input values of a given input/output mapping (e.g., numerical values associated with data inputs) are input to the neural network, and output values (e.g., numerical values associated with target outputs) of the input/output mapping are stored in the output nodes of the neural network. The connection weights in the neural network are then adjusted in accordance with a learning algorithm (e.g., back propagation, etc.), and the procedure is repeated for the other input/output mappings in data set T. After block 507, machine learning model (e.g., machine learning model 190) can be at least one of trained using training engine 182 of server machine 180, validated using validating engine 184 of server machine 180, or tested using testing engine 186 of server machine 180. The trained machine learning model may be implemented by action prescription component 194 (of server machine 192) to identify a prescriptive action based on a cell growth data.

In some embodiments, a training dataset that was generated is used to train a machine learning model and/or a physical model. The model may be trained to receive as an input cell growth data. The model may output a prescriptive action to be performed by a cell growth system to alter a target output formation by a cell culture associated with the cell growth data. In embodiments, the model may be agnostic to cell growth chamber and/or to cell growth recipes. Accordingly, the model may be generated based on training data items generated based on processes run on a first cell cultivation system or first set of growth recipes, and may then be used for a second cell cultivation system without performing any transfer learning to tune the model for the second cell cultivation system.

In one embodiment, the trained machine learning model is a regression model trained using regression. Examples of regression models are regression models trained using linear regression or Gaussian regression. A regression model predicts a value of Y given known values of X variables. The regression model may be trained using regression analysis, which may include interpolation and/or extrapolation. In one embodiment, parameters of the regression model are estimated using least squares. Alternatively, Bayesian linear regression, percentage regression, leas absolute deviations, nonparametric regression, scenario optimization and/or distance metric learning may be performed to train the regression model.

In one embodiment, the trained machine learning model is a decision tree, a random forest model, a support vector machine, or other type of machine learning model.

In one embodiment, the trained machine learning model is an artificial neural network (also referred to simply as a neural network). The artificial neural network may be, for example, a convolutional neural network (CNN) or a deep neural network. In one embodiment, processing logic performs supervised machine learning to train the neural network.

Artificial neural networks generally include a feature representation component with a classifier or regression layers that map features to a target output space. A convolutional neural network (CNN), for example, hosts multiple layers of convolutional filters. Pooling is performed, and non-linearities may be addressed, at lower layers, on top of which a multi-layer perceptron is commonly appended, mapping top layer features extracted by the convolutional layers to decisions (e.g. classification outputs). The neural network may be a deep network with multiple hidden layers or a shallow network with zero or a few (e.g., 1-2) hidden layers. Deep learning is a class of machine learning algorithms that use a cascade of multiple layers of nonlinear processing units for feature extraction and transformation. Each successive layer uses the output from the previous layer as input. Neural networks may learn in a supervised (e.g., classification) and/or unsupervised (e.g., pattern analysis) manner. Some neural networks (e.g., such as deep neural networks) include a hierarchy of layers, where the different layers learn different levels of representations that correspond to different levels of abstraction. In deep learning, each level learns to transform its input data into a slightly more abstract and composite representation.

Training of a neural network may be achieved in a supervised learning manner, which involves feeding a training dataset consisting of labeled inputs through the network, observing its outputs, defining an error (by measuring the difference between the outputs and the label values), and using techniques such as deep gradient descent and back-propagation to tune the weights of the network across all its layers and nodes such that the error is minimized. In many applications, repeating this process across the many labeled inputs in the training dataset yields a network that can produce correct output when presented with inputs that are different than the ones present in the training dataset. In data volume settings, such as involved cell cultivation system, this generalization is achieved when a sufficiently large and diverse training dataset is made available.

The trained machine learning model may be periodically or continuously retrained to achieve continuous learning and improvement of the trained machine learning model. The model may generate an output based on an input, an action may be performed based on the output, and a result of the action may be measured. In some instances, the result of the action is measured within seconds or minutes, and in some instances, it takes longer to measure the result of the action. For example, one or more additional processes may be performed before a result of the action can be measured. The action and the result of the action may indicate whether the output was a correct output and/or a difference between what the output should have been and what the output was. Accordingly, the action and the result of the action may be used to determine a target output that can be used as a label for the sensor measurements. Once the result of the action is determined, the input (e.g., cell growth data), the output of the trained machine learning model (e.g., prescriptive action), and the target result (e.g., target product formation yield) actual measured result (e.g., measured product formation yield) may be used to generate a new training data item. The new training data item may then be used to further train the trained machine learning model. This retraining process may be performed on-tool on the cell cultivation system in some embodiments.

FIG. 6A-B depict flow diagrams of methods 600A-B associated with determining measurement accuracy of sensors, according to certain embodiments. Methods 600A-B may be performed by processing logic that may include hardware (e.g., circuitry, dedicated logic, programmable logic, microcode, processing device, etc.), software (such as instructions run on a processing device, a general purpose computer system, or a dedicated machine), firmware, microcode, or a combination thereof. In some embodiments, methods 600A-C may be performed, in part, by machine learning system 170 (e.g. server machine 172, server machine 180, server machine 192, sensor accuracy component 196, etc.) Machine learning system 170 may use method 600A to train a machine learning model, in accordance with embodiments of the disclosure. Machine learning system 170 may use method 600B to use a trained machine learning model, in accordance with embodiments of the disclosure. In some embodiments, one or more operations of methods 600A-B may be performed by sensor accuracy component 196 of server machine 192 as described with respects to FIG. 1. It may be noted that component 196 described with response to one or more of FIGS. 1-3 may be used to illustrate aspects of FIGS. 6A-B. In some embodiments, a non-transitory storage medium stores instruction that when executed by a process device (e.g., of machine learning system 170) cause the processing device to perform methods 600A-B.

Referring to FIG. 6A, method 600A is associated with training a machine learning model for determining measurement accuracy of a sensor (e.g., a PAT sensor).

At block 601, processing logic identifies first metrology data measured using a first sensor (e.g., a first PAT sensor). The first metrology data may include raw measured cell growth data, as described in associated with other figures. As discussed in FIGS. 1-2, the metrology data may be engineered data or data that has undergone a feature extraction to create synthetic data. The sets of metrology data may be historical data corresponding to cell cultures that have previously been cultivated.

In some embodiments, at block 602, processing logic identifies accuracy data corresponding to the first metrology data. In some embodiments, the accuracy data indicates whether measurements (e.g., environmental condition, critical process parameters, and growth input parameter values) of the cell cultivation system associated with the metrology data meet threshold measurements (e.g., whether they are good or bad).

At block 603, processing logic trains a machine learning model using data input including the first metrology data (e.g., and target output including the performance data) to generate a trained machine learning model configured to generate outputs to cause performance of a prescriptive action associated with a cell cultivation system.

In some embodiments, the machine learning model is trained based on data input (e.g., without target output) to generate an unsupervised trained machine learning model (e.g., to cluster data). In some embodiments, the machine learning model is trained based on data input and target output to generate a supervised trained machine learning model. For example the trained machine learning model may be a model trained using principal component analysis (PCA) or with support vectors.

Referring to FIG. 6B, method 600B is associated with using a machine learning model for determining measurement accuracy of a metrology tool (e.g., a sensor).

At block 611, processing logic receives current data. In some embodiments, the current data is metrology data taken by a sensor measuring growth data or a current cell culture (e.g., for which there is not performance data). In some embodiments, the current data includes sensor data, metrology data, and/or synthetic data.

At block 612, processing logic provides the current data (e.g., metrology data) to a trained machine learning model. The trained machine learning model may be trained by method 600B.

At block 613, processing logic obtains, from the trained machine learning model, one or more outputs indicative of measurement accuracy of a sensor associated with the metrology data used as input to the trained machine learning model. In some embodiments, the measurement accuracy is predictive performance data (e.g., whether the sensor is good or bad, whether the data is good or bad) (e.g., result from a supervised machine learning model). In some embodiments, the measurement accuracy is an indication of similarity between historical data and the current data (e.g., the historical data and current data are part of the same cluster, the current data is not clustered with any of the historical data) (e.g., result from an unsupervised machine learning model).

At block 614, processing logic determines, based on the measurement accuracy, whether the sensor meets a threshold criterion. For example, the sensor accuracy may include a determination that the sensor is the most accurate of sensor in a collection of sensor. In another example, the sensor accuracy may include a determination that the sensor meets a minimum accuracy standard.

Figure 7:
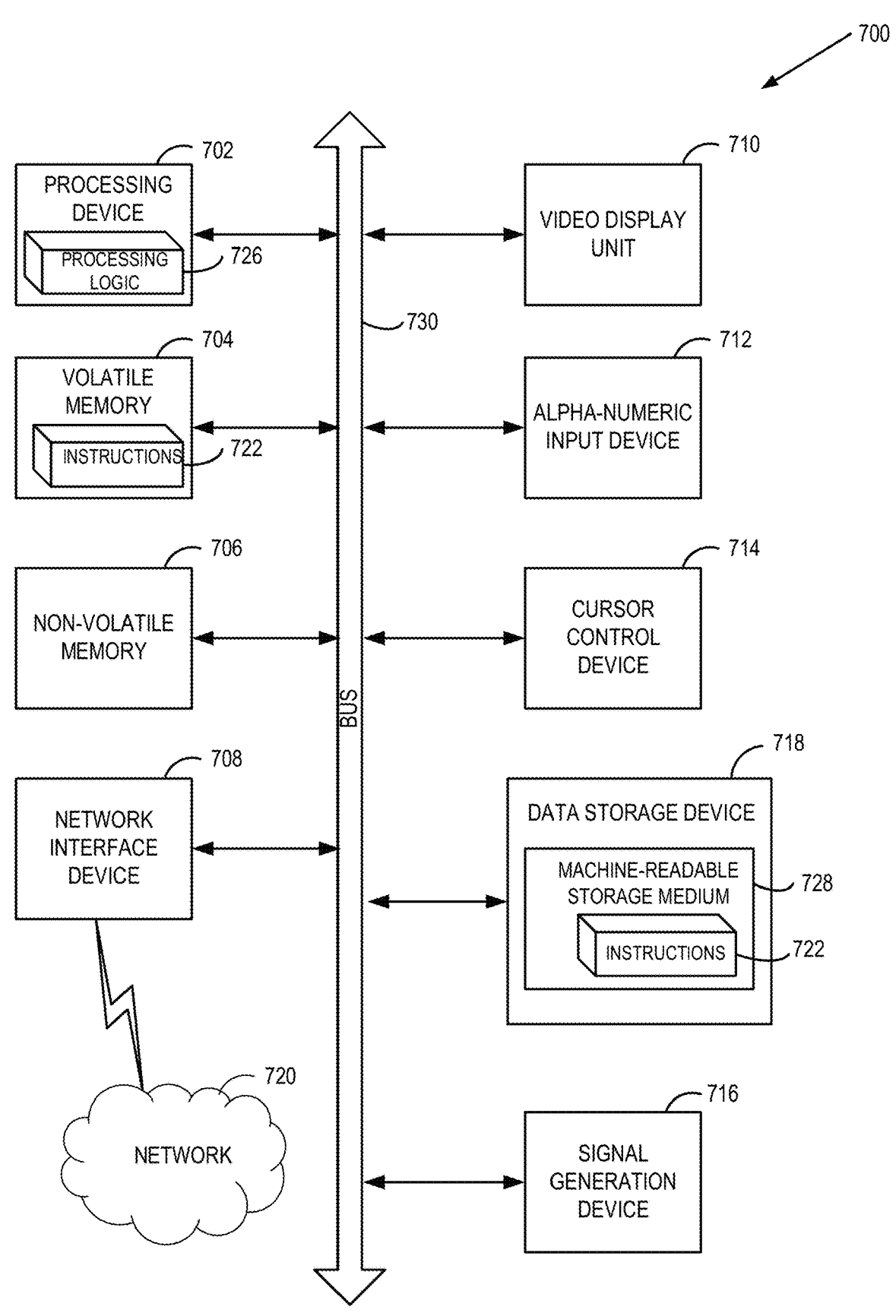
FIG. 7 depicts a block diagram of an example computing device, operating in accordance with one or more aspects of the present disclosure.

FIG. 7 depicts a block diagram of an example computing device 700, operating in accordance with one or more aspects of the present disclosure. In various illustrative examples, various components of the computing device 700 may represent various components of the client devices 150, metrology system 110, server, 120, data store 140, and machine learning system 170, illustrated in FIG. 1.

Example computing device 700 may be connected to other computer devices in a LAN, an intranet, an extranet, and/or the Internet. Computing device 700 may operate in the capacity of a server in a client-server network environment. Computing device 700 may be a personal computer (PC), a set-top box (STB), a server, a network router, switch or bridge, or any device capable of executing a set of instructions (sequential or otherwise) that specify actions to be taken by that device. Further, while only a single example computing device is illustrated, the term "computer" shall also be taken to include any collection of computers that individually or jointly execute a set (or multiple sets) of instructions to perform any one or more of the methods discussed herein.

Example computing device 700 may include a processing device 702 (also referred to as a processor or CPU), a main memory 704 (e.g., read-only memory (ROM), flash memory, dynamic random access memory (DRAM) such as synchronous DRAM (SDRAM), etc.), a static memory 706 (e.g., flash memory, static random access memory (SRAM), etc.), and a secondary memory (e.g., a data storage device 718), which may communicate with each other via a bus 730.

Processing device 702 represents one or more general-purpose processing devices such as a microprocessor, central processing unit, or the like. More particularly, processing device 702 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. In accordance with one or more aspects of the present disclosure, processing device 702 may be configured to execute instructions implementing methods 400-600A-B illustrated in FIGS. 4-6.

Example computing device 700 may further comprise a network interface device 708, which may be communicatively coupled to a network 720. Example computing device 700 may further comprise a video display 710 (e.g., a liquid crystal display (LCD), a touch screen, or a cathode ray tube (CRT)), an alphanumeric input device 712 (e.g., a keyboard), a cursor control device 714 (e.g., a mouse), and an acoustic signal generation device 716 (e.g., a speaker).

Data storage device 718 may include a machine-readable storage medium (or, more specifically, a non-transitory machine-readable storage medium) 728 on which is stored one or more sets of executable instructions 722. In accordance with one or more aspects of the present disclosure, executable instructions 722 may comprise executable instructions associated with executing methods 400-600A-B illustrated in FIGS. 4-6.

Executable instructions 722 may also reside, completely or at least partially, within main memory 704 and/or within processing device 702 during execution thereof by example computing device 700, main memory 704 and processing device 702 also constituting computer-readable storage media. Executable instructions 722 may further be transmitted or received over a network via network interface device 708.

While the computer-readable storage medium 728 is shown in FIG. 7 as a single medium, the term "computer-readable storage medium" should be taken to include a single medium or multiple media (e.g., a centralized or distributed database, and/or associated caches and servers) that store the one or more sets of operating instructions. The term "computer-readable storage medium" shall also be taken to include any medium that is capable of storing or encoding a set of instructions for execution by the machine that cause the machine to perform any one or more of the methods described herein. The term "computer-readable storage medium" shall accordingly be taken to include, but not be limited to, solid-state memories, and optical and magnetic media.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "identifying," "determining," "storing," "adjusting," "causing," "returning," "comparing," "creating," "stopping," "loading," "copying," "throwing," "replacing," "performing," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Examples of the present disclosure also relate to an apparatus for performing the methods described herein. This apparatus may be specially constructed for the required purposes, or it may be a general purpose computer system selectively programmed by a computer program stored in the computer system. Such a computer program may be stored in a computer readable storage medium, such as, but not limited to, any type of disk including optical disks, compact disc read only memory (CD-ROMs), and magnetic-optical disks, read-only memories (ROMs), random access memories (RAMs), erasable programmable read-only memory (EPROMs), electrically erasable programmable read-only memory (EEPROMs), magnetic disk storage media, optical storage media, flash memory devices, other type of machine-accessible storage media, or any type of media suitable for storing electronic instructions, each coupled to a computer system bus.

The methods and displays presented herein are not inherently related to any particular computer or other apparatus. Various general purpose systems may be used with programs in accordance with the teachings herein, or it may prove convenient to construct a more specialized apparatus to perform the required method steps. The required structure for a variety of these systems will appear as set forth in the description below. In addition, the scope of the present disclosure is not limited to any particular programming language. It will be appreciated that a variety of programming languages may be used to implement the teachings of the present disclosure.

It is to be understood that the above description is intended to be illustrative, and not restrictive. Many other implementation examples will be apparent to those of skill in the art upon reading and understanding the above description. Although the present disclosure describes specific examples, it will be recognized that the systems and methods of the present disclosure are not limited to the examples described herein, but may be practiced with modifications within the scope of the appended claims. Accordingly, the specification and drawings are to be regarded in an illustrative sense rather than a restrictive sense. The scope of the present disclosure should, therefore, be determined with reference to the appended claims, along with the full scope of equivalents to which such claims are entitled.

What is claimed is:

1. A method, comprising:

receiving cell growth data associated with a current cell culture of a cell growth system, the cell growth data comprising:

growth input parameter values indicative of a growth rate of the current cell culture, and process analytical technology (PAT) sensor data comprising indications of one or more of cell count, density, or target product formation;

providing the cell growth data to a mechanistic model as input;

obtaining, from the mechanistic model, mechanistic output comprising a prediction of future conditions of the current cell culture based on the cell growth data;

providing the cell growth data to a statistical model;

obtaining, from the statistical model, statistical output comprising relationships in the cell growth data and historical cell growth data based on the cell growth data;

identifying, using a first machine learning model, a prescriptive action to alter a yield of a target product of the current cell culture based on the mechanistic output and the statistical output, wherein the prescriptive action modifies a metabolism rate of the current cell culture, the prescriptive action comprising an adjustment to at least one of feed flow rate, air flow rate, agitation rate, applied heat, applied pressure, or oxygen flow rate;

identifying, using the first machine learning model, a first level of confidence that the prescriptive action, when performed, alters the yield of the target product; and causing the cell growth system to perform the identified prescriptive action in view of the first level of confidence.

2. The method of claim 1, further comprising:

using the cell growth data as input to the first machine learning model; and obtaining one or more outputs of the machine learning model, the one or more outputs indicating (i) the prescriptive action, and (ii) the level of confidence that the prescriptive action, when performed, alters the yield of the target product; and determining that the level of confidence for the prescriptive action satisfies a threshold condition.

3. The method of claim 1, further comprising:

applying a growth prediction model to the cell growth data to generate a predicted cell density of the current cell culture, wherein the growth prediction model is generated using one or more cell counts of one or more previous cell cultures in the cell growth system and one or more historical growth input parameter values indicative of a previous growth rate of each of the one or more previous cell cultures in the cell growth system; and using the predicted cell density as input to the first machine learning model.

4. The method of claim 3, wherein the growth prediction model comprises the mechanistic model generated by performing at least an exponential regression using the one or more historical growth input parameter values.

5. The method of claim 1 further comprising:

receiving, from a first sensor, first sensor data indicative of an environmental condition of a growth environment of the current cell culture in the cell growth system; and using the first sensor data as input to the first machine learning model.

6. The method of claim 5, further comprising processing the first sensor data using the statistical model by performing one of a process control analysis, univariate limit violation analysis, or a multivariate limit violation analysis on the first sensor data, wherein the first sensor comprises a process analytical technology (PAT) sensor.

7. The method of claim 5, further comprising:

receiving, from a second sensor, second sensor data indicative of the environmental condition of the growth environment of the current cell culture;

using the first sensor data and the second sensor data as input to a second machine learning model;

obtaining one or more outputs of the second machine learning model, the one or more outputs indicating a second level of confidence that a first measurement accuracy of the first sensor data is greater than a second accuracy of the second sensor;

determining that the second level of confidence that the first measurement accuracy of the first sensor data is greater than the second accuracy of the second sensor satisfies a threshold condition; and providing an indication of the second level of confidence to the first machine learning model, wherein at least one of identifying the prescriptive action or identifying the first level of confidence is based on the second level of confidence.

8. The method of claim 7, where the second machine learning model comprises a principal component analysis (PCA) model.

9. The method of claim 1, wherein the growth input parameter values comprises a value indicative of at least one of a feed flow rate, an airflow rate, or an oxygen flow rate to the current cell culture.

10. The method of claim 1, wherein the first machine learning model comprises at least one of a random forest decision tree model, a partial least squares regression (PLS) model, or a multivariate statistical process control (MVSPC) model.

11. The method of claim 1, further comprising:
providing the cell growth data to a machine learning feature extractor model configured to generate synthetic data based on cell growth data; and
obtaining dimensionally reduced data from the machine learning feature extractor model based on the cell growth data, wherein identifying the prescriptive action is further based on the dimensionally reduced data.

12. The method of claim 11, further comprising: providing the cell growth data to the first machine learning model, wherein identifying the prescriptive action is further based on the cell growth data.

13. A non-transitory machine-readable storage medium comprising instructions that, when executed by a processing device, cause the processing device to perform operations comprising:
receive cell growth data associated with a current cell culture of a cell growth system, the cell growth data comprising:
growth input parameter values indicative of a growth rate of the current cell culture, and
process analytical technology (PAT) sensor data comprising indications of one or more of cell count, density, or target product formation;
provide the cell growth data to a mechanistic model as input;
obtain, from the mechanistic model, mechanistic output comprising a prediction of future conditions of the current cell culture based on the cell growth data;
provide the cell growth data to a statistical model;
obtain, from the statistical model, statistical output comprising relationships in the cell growth data and historical cell growth data;
identify, using a first machine learning model, a prescriptive action to alter a yield of a target product of the current cell culture based on the mechanistic output and the statistical output, wherein the prescriptive action modifies a metabolism rate of the current cell culture based on the cell growth data, the prescriptive action comprising an adjustment to at least one of feed flow rate, air flow rate, agitation rate, applied heat, applied pressure, or oxygen flow rate;
identify, using the first machine learning model, a first level of confidence that the prescriptive action, when performed, alters the yield of the target product; and
cause the cell growth system to perform the identified prescriptive action in view of the first level of confidence.

14. The non-transitory machine-readable storage medium of claim 13, the operations further comprising:

use the cell growth data as input to the first machine learning model; and
obtain one or more outputs of the machine learning model, the one or more outputs indicating (i) the prescriptive action, and (ii) the level of confidence that the prescriptive action, when performed, alters the yield of the target product; and
determine that the level of confidence for the prescriptive action satisfies a threshold condition.

15. The non-transitory machine-readable storage medium of claim 13, the operations further comprising:
apply a growth prediction model to the cell growth data to generate a predicted viable cell density of the cell culture, wherein the growth prediction model is generated using one or more cell counts of one or more previous cell cultures in the cell growth system and one or more historical growth input parameter values indicative of a growth rate of each of the one or more previous cell cultures in the cell growth system; and
use the predicted viable cell density as input to the first machine learning model.

16. The non-transitory machine-readable storage medium of claim 13, the operations further comprising:
receive from a first sensor, first sensor data indicative of an environmental condition of a growth environment of the current cell culture in the cell growth system; and
use the first sensor data as input to the first machine learning model.

17. The non-transitory machine-readable storage medium of claim 16, the operations further comprising:
process the first sensor data by performing one of a process control analysis, univariate limit violation analysis, or a multivariate limit violation analysis on the first sensor data, wherein the first sensor comprises a process analytical technology (PAT) sensor.

18. The non-transitory machine-readable storage medium of claim 16, the operations further comprising:
receive, from a second sensor, second sensor data indicative of the environmental condition of the growth environment of the current cell culture;
use the first sensor data and the second sensor data as input to a second machine learning model;
obtain one or more outputs of the second machine learning model, the one or more outputs indicating a second level of confidence that a first measurement accuracy of the first sensor data is greater than a second accuracy of the second sensor;
determine that the second level of confidence that the first measurement accuracy of the first sensor data is greater than the second accuracy of the second sensor satisfies a threshold condition; and
provide an indication of the second level of confidence to the first machine learning model, wherein at least one of identifying the prescriptive action or identifying the first level of confidence is based on the second level of confidence.

* * * * *